United States Patent
Kawase et al.

(10) Patent No.: US 10,885,330 B2
(45) Date of Patent: Jan. 5, 2021

(54) IMAGE PROCESSING APPARATUS, IMAGE PROCESSING METHOD, AND STORAGE MEDIUM

(71) Applicant: CANON KABUSHIKI KAISHA, Tokyo (JP)

(72) Inventors: Daisuke Kawase, Ichikawa (JP); Hiroki Uchida, Tokyo (JP); Osamu Sagano, Inagi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 52 days.

(21) Appl. No.: 16/119,892

(22) Filed: Aug. 31, 2018

(65) Prior Publication Data
US 2019/0073532 A1 Mar. 7, 2019

(30) Foreign Application Priority Data

Sep. 6, 2017 (JP) .................................. 2017-171188

(51) Int. Cl.
*G06K 9/00* (2006.01)
*G06T 11/00* (2006.01)
(Continued)

(52) U.S. Cl.
CPC .......... *G06K 9/00604* (2013.01); *A61B 3/102* (2013.01); *G06T 7/579* (2017.01); *G06T 11/005* (2013.01); *G06T 2207/10012* (2013.01); *G06T 2207/10101* (2013.01); *G06T 2207/20221* (2013.01); *G06T 2207/30041* (2013.01); *G06T 2207/30201* (2013.01); *G06T 2211/404* (2013.01)

(58) Field of Classification Search
None
See application file for complete search history.

(56) References Cited

U.S. PATENT DOCUMENTS 7,744,221 B2 * 6/2010 Wei ........................ A61B 3/102
351/200
10,010,249 B1 * 7/2018 Sadda .................. A61B 3/1241
(Continued)

FOREIGN PATENT DOCUMENTS

JP 2017-47113 A 3/2017
WO 2017/218738 A1 12/2017

OTHER PUBLICATIONS

Nagpal et al "Panoramic Imaging with OctA" Retina today, Apr. 2017 (Year: 2017).*

*Primary Examiner* — Shervin K Nakhjavan
(74) *Attorney, Agent, or Firm* — Canon U.S.A., Inc. IP Division

(57) ABSTRACT

An image processing apparatus capable of easily generating a two-dimensional panoramic image at a high speed from a plurality of three-dimensional images includes an acquisition unit configured to acquire a generation condition of a first en-face image generated from a first three-dimensional image of an target eye, a first generation unit configured to generate a second en-face image from a second three-dimensional image of the target eye by applying the generation condition acquired by the acquisition unit to the second three-dimensional image, and a second generation unit configured to generate a combined image by combining the first en-face image with the second en-face image.

14 Claims, 11 Drawing Sheets

(51) Int. Cl.
  *G06T 7/579* (2017.01)
  *A61B 3/10* (2006.01)

(56) References Cited

U.S. PATENT DOCUMENTS

| | | | |
|---|---|---|---|
| 2008/0088852 A1* | 4/2008 | Rogers | G01B 9/0203 356/497 |
| 2008/0100612 A1* | 5/2008 | Dastmalchi | A61B 3/102 345/418 |
| 2008/0170204 A1* | 7/2008 | Podoleanu | A61B 3/102 351/206 |
| 2012/0002856 A1* | 1/2012 | McLean | A61B 3/1225 382/131 |
| 2013/0045203 A1* | 2/2013 | Joshi | A61K 31/192 424/133.1 |
| 2013/0176532 A1* | 7/2013 | Sharma | A61B 3/102 351/206 |
| 2015/0092195 A1* | 4/2015 | Blatter | A61B 5/6821 356/479 |
| 2015/0374228 A1* | 12/2015 | Satake | G06T 7/0016 351/206 |
| 2016/0227999 A1 | 8/2016 | An | |
| 2016/0278627 A1* | 9/2016 | Huang | A61B 3/0041 |
| 2017/0035286 A1* | 2/2017 | Meyer | A61B 3/102 |
| 2017/0065170 A1 | 3/2017 | Yamashita | |
| 2018/0014728 A1* | 1/2018 | An | G06T 7/0014 |
| 2018/0020909 A1* | 1/2018 | Jia | A61B 3/1233 351/206 |
| 2018/0078130 A1* | 3/2018 | Charles | A61B 3/0025 |

* cited by examiner

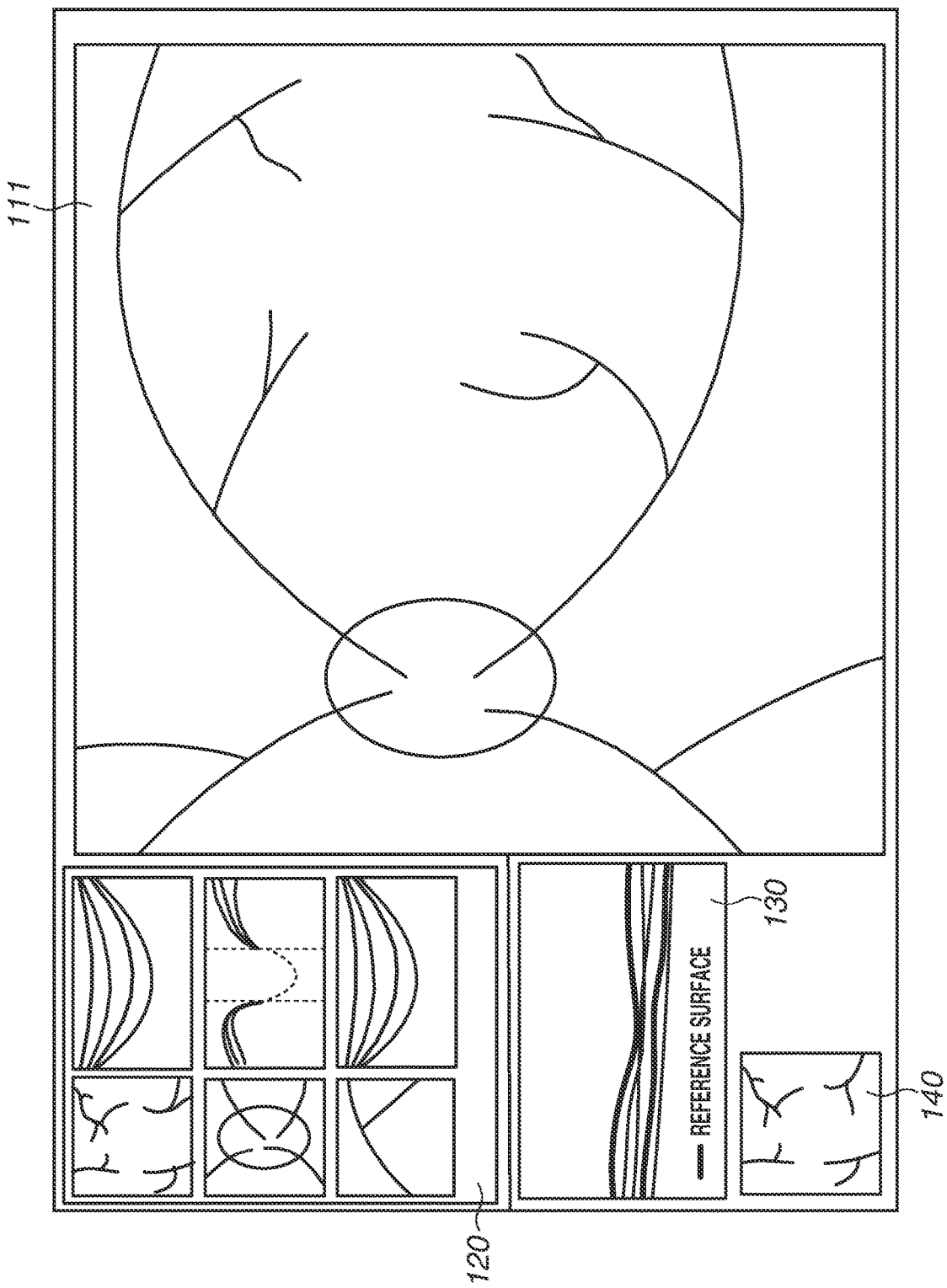

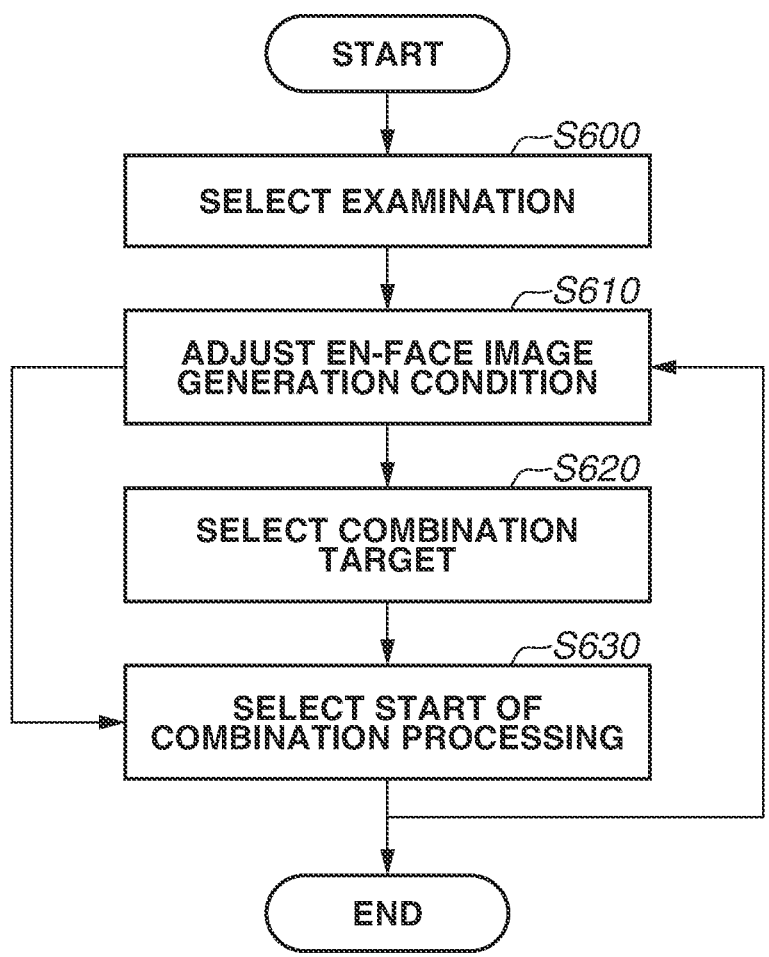

IMAGE PROCESSING APPARATUS, IMAGE PROCESSING METHOD, AND STORAGE MEDIUM

BACKGROUND OF THE INVENTION

Field of the Invention

The present invention relates to an image processing apparatus, image processing method, and a storage medium.

Description of the Related Art

As an apparatus for observing a target eye (i.e., eye to be examined), an optical Coherence Tomography (OCT) is known. Further, it is known that a two-dimensional image is generated from a three-dimensional image acquired by using the OCT. The two-dimensional image is called an en-face image obtained by projecting, in a depth direction, pixels in a range located between any two reference surfaces different in a depth position. Further, Japanese Patent Application Laid-Open No. 2017-47113 discusses generation of a two-dimensional panoramic image by combining a plurality of en-face images acquired by using an OCT angiography (OCTA).

However, generation of a two-dimensional combined image such as a two-dimensional panoramic image places a burden on a user. This is because in order to generate a plurality of two-dimensional images as sources of the combined image, it is necessary that, for example, the user sets generation conditions of the two-dimensional images for a plurality of three-dimensional images, such as a reference surface.

The present disclosure is directed to a technique for easily generating a two-dimensional combined image from a plurality of three-dimensional images.

Not limited to the above object, the present disclosure includes operations and effects that are to be derived by configurations in exemplary embodiments of the present invention described below and cannot be obtained by conventional techniques.

SUMMARY OF THE INVENTION

According to an aspect of the present invention, an image processing apparatus includes an acquisition unit configured to acquire a generation condition of a first en-face image generated from a first three-dimensional image of a target eye, a first generation unit configured to generate a second en-face image from a second three-dimensional image of the target eye by applying the generation condition acquired by the acquisition unit to the second three-dimensional image, and a second generation unit configured to generate a combined image by combining the first en-face image with the second en-face image.

Further features of the present invention will become apparent from the following description of exemplary embodiments with reference to the attached drawings.

BRIEF DESCRIPTION OF THE DRAWINGS

FIG. 10 is a diagram illustrating an example of a display screen of an image processing apparatus according to a fourth exemplary embodiment.

FIG. 11 is a flowchart illustrating an example of an operation of the image processing apparatus according to the fourth exemplary embodiment.

DESCRIPTION OF THE EMBODIMENTS

Figure 1:
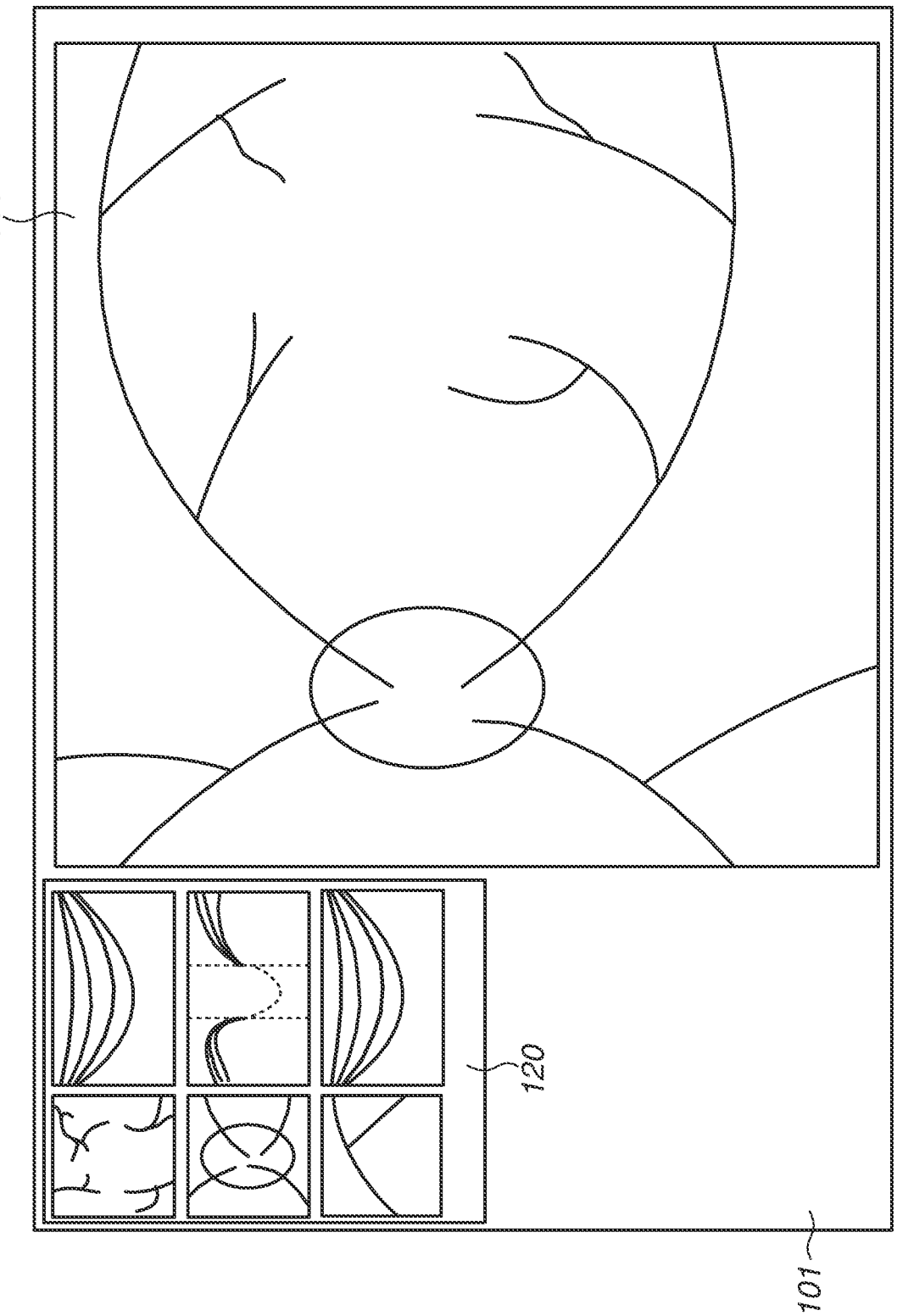
FIG. 1 is a diagram illustrating an example of a display screen of an image processing apparatus according to a first exemplary embodiment.

Exemplary embodiments will be described below with reference to the drawings. The same or similar components, members, and processing illustrated in the drawings are denoted by the same numerals or symbols, and overlapped description is suitably omitted. Further, in the drawings, components, members and processing that are not important for the description are partially omitted in some cases. Each of the embodiments of the present invention described below can be implemented solely or as a combination of a plurality of the embodiments or features thereof where necessary or where the combination of elements or features from individual embodiments in a single embodiment is beneficial.

Figure 2:
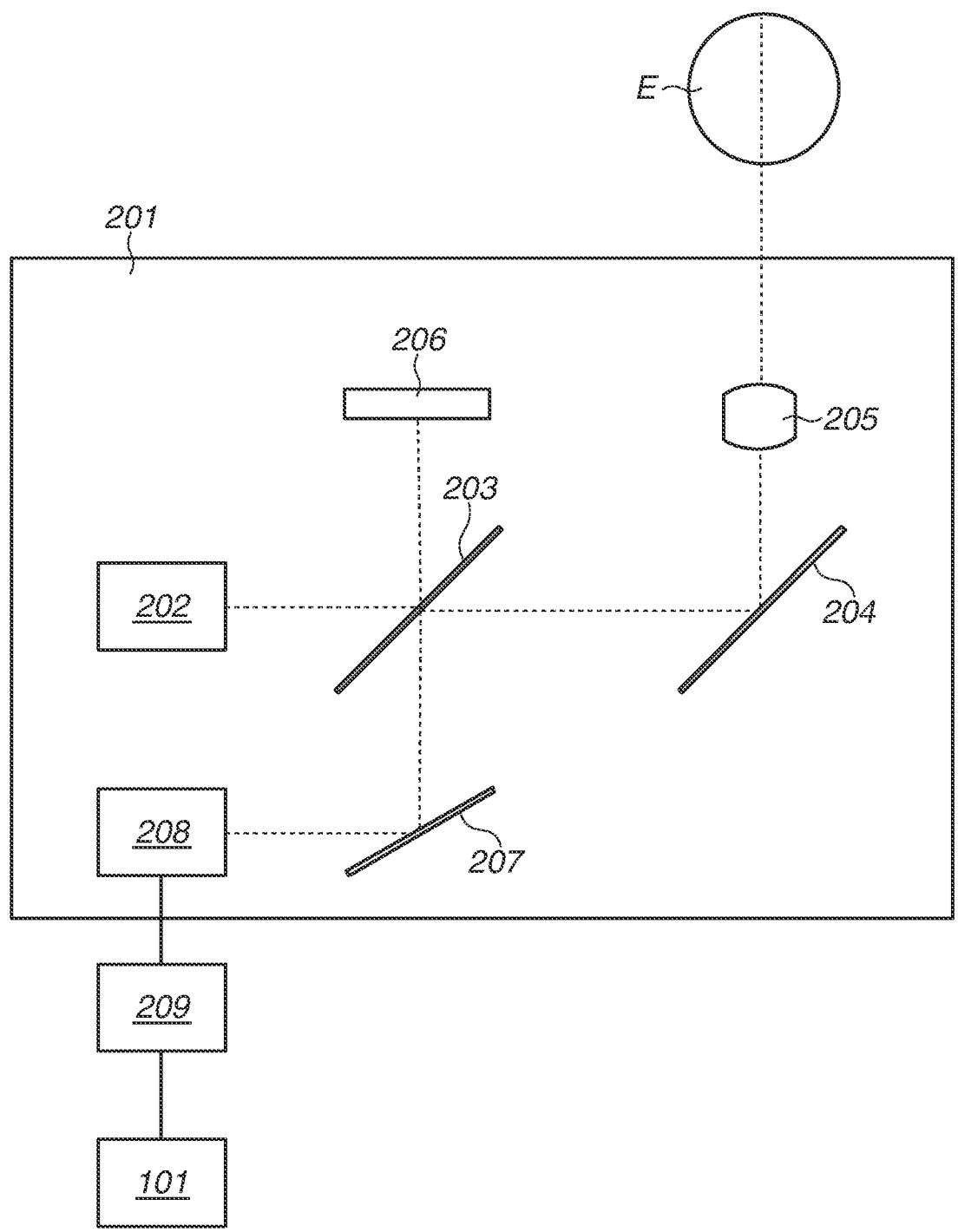
FIG. 2 is a diagram illustrating an example of a configuration of an image processing system according to the first exemplary embodiment.

FIG. 2 is a diagram illustrating an example of a configuration of an image processing system according to a first exemplary embodiment. The image processing system according to the first exemplary embodiment includes an optical coherence tomography (OCT) image capturing apparatus 201, an image processing apparatus 209, and a display apparatus 101. In FIG. 2, the OCT image capturing apparatus 201, the image processing apparatus 209, and the display apparatus 101 are separated, but the configuration is not limited to this form, and for example, the image processing apparatus 209 and the display apparatus 101 may be configured to be integrated. Further, the OCT image capturing apparatus 201 and the image processing apparatus 209 may be configured to be integrated.

The OCT image capturing apparatus 201 acquires a signal representing a tomographic image of a target eye (i.e., eye to be examined) E based on a two-dimensional measurement range specified on, for example, an eye fundus surface of the target eye E and measurement depth information. The OCT image capturing apparatus 201 is, for example, a spectral-domain OCT (SD-OCT), but any OCT system can be employed as long as the OCT can capture an image of a fault of the target eye E. As illustrated in FIG. 2, the OCT image capturing apparatus 201 includes a light source 202, a half mirror 203, a galvano mirror 204, an object lens 205, a reference mirror 206, a diffractive grating 207, and a line sensor 208.

Low coherence light emitted from the light source 202 is divided into measurement light and reference light by the half mirror 203. Measurement light enters a target eye E via the galvano mirror 204 and the object lens 205. A scanning position of the target eye E can be changed by driving the galvano mirror 204. In FIG. 2, for simplification, only the one galvano mirror 204 is illustrated, but actually two galvano mirrors that can scan light in mutually orthogonal directions are used. The measurement light that has entered the target eye E is reflected and scattered by the target eye E. Then, the measurement light then returns to the half mirror 203 along a reverse optical path. The reference light is reflected by the reference mirror 206. Then, the reference light returns to the half mirror 203 along a reverse optical path. The half mirror 203 overlaps a return light of the measurement light and a return light of the reference light to generate interference light. The diffractive grating 207 disperses the interference light into wavelength components from wavelengths $\lambda 1$ to $\lambda n$. The line sensor 208 detects the dispersed interference light for each of the wavelength components. The line sensor 208 outputs signal according to a detected result.

Figure 3:
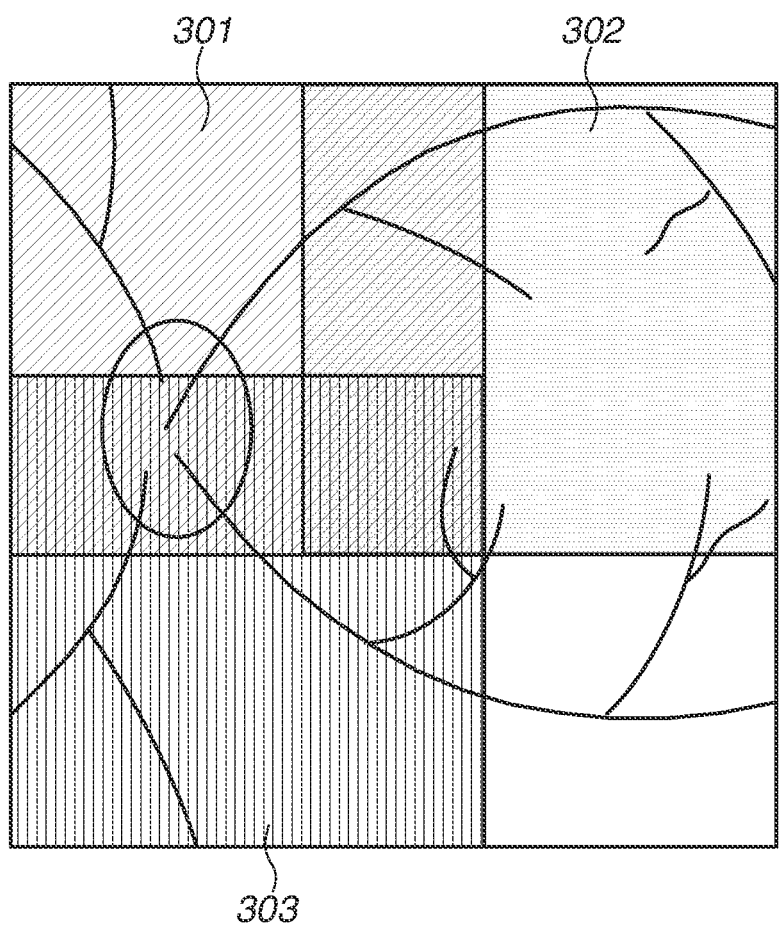
FIG. 3 is a diagram illustrating an example of an image acquisition method according to the first exemplary embodiment.

The OCT image capturing apparatus 201 according to the present exemplary embodiment has a panoramic imaging mode as a mode for sequentially acquiring tomographic images of different portions of the target eye E. In a case where an operator selects this mode, after the imaging of a partial region 301 of the target eye E illustrated in FIG. 3 is completed, for example, a visual line of the target eye E is guided to a different direction by moving an internal fixation lamp. The imaging in this state makes it possible to acquire a tomographic image of a partial region 302 different from the tomographic image of the partial region 301. A tomographic image of a residual partial region 303 can be acquired by sequentially executing the similar processing. In a case where a wide-angle panoramic combined image based on the tomographic image captured in the panoramic imaging mode is generated, it is desirable to move the internal fixation lamp so that adjacent regions (e.g., the partial region 301 and the partial region 302) are at least partially overlapped with each other. In the present exemplary embodiment, the internal fixation lamp is moved so that the partial region 301 and the partial region 302 are overlapped with each other by 25% of areas. The numerical value is an example and thus is not limited to the example.

The image processing apparatus 209 is, for example, a computer. The image processing apparatus 209 generates a tomographic image of, for example, an eye fundus of the target eye E by using Fourier transformation, based on an output signal from the line sensor 208. Since the method for generating a tomographic image can be realized by a known method, detailed description thereof is omitted.

Emission of measurement light to any point of the target eye E is referred to as "A scan" in the present exemplary embodiment, and a tomographic image generated by the A scan is referred to as an "A-scan image" in some cases. Further, intermittent emission of measurement light to the target eye E along any scanning line is referred to as "B scan", and a tomographic image acquired by the B scan is referred to as a "B-scan image" in some cases. In this way, the B-scan image is configured by a plurality of A-scan images.

The image processing apparatus 209 acquires B-scan images of a plurality of portions of the target eye E to be able to configure a three-dimensional image of the target eye E. A B-scan direction may be a radial scan direction where a specific portion is radially scanned, or a horizontal scan direction or a vertical scan direction where a specific portion is scanned in a certain one direction.

Figure 4:
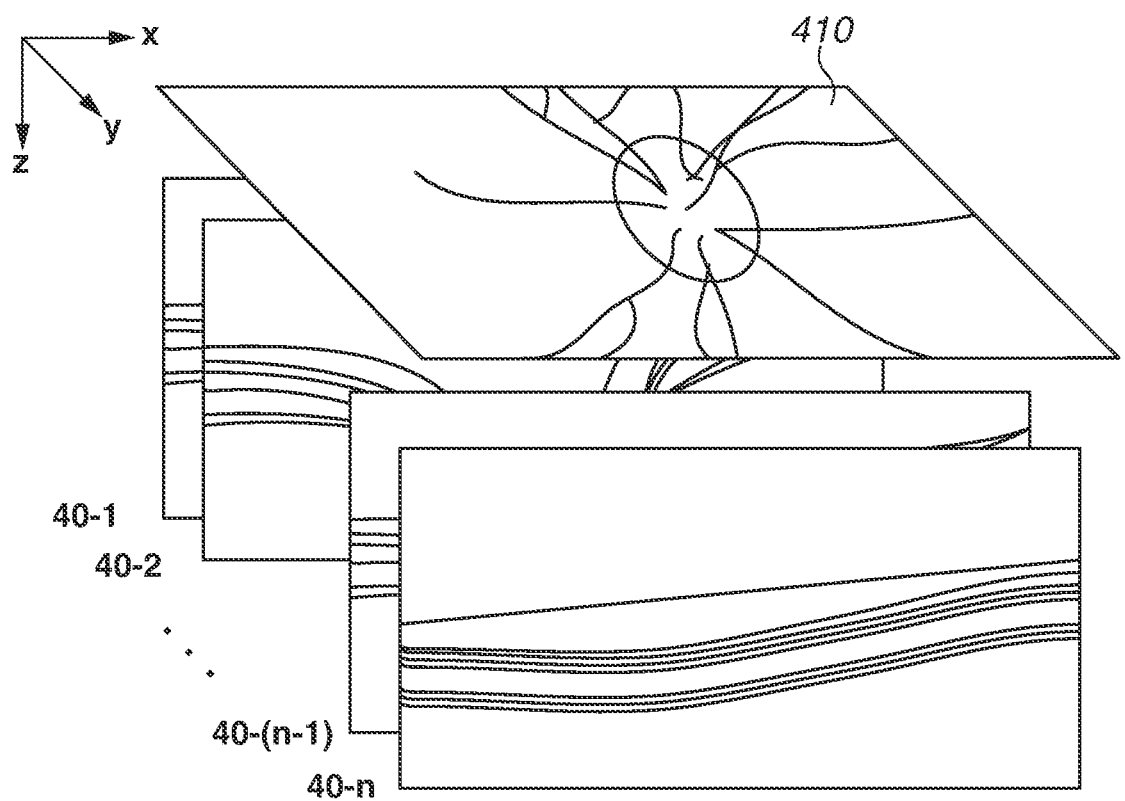
FIG. 4 is a diagram illustrating an example of a method for generating an en-face image according to the first exemplary embodiment.
Figure 7:
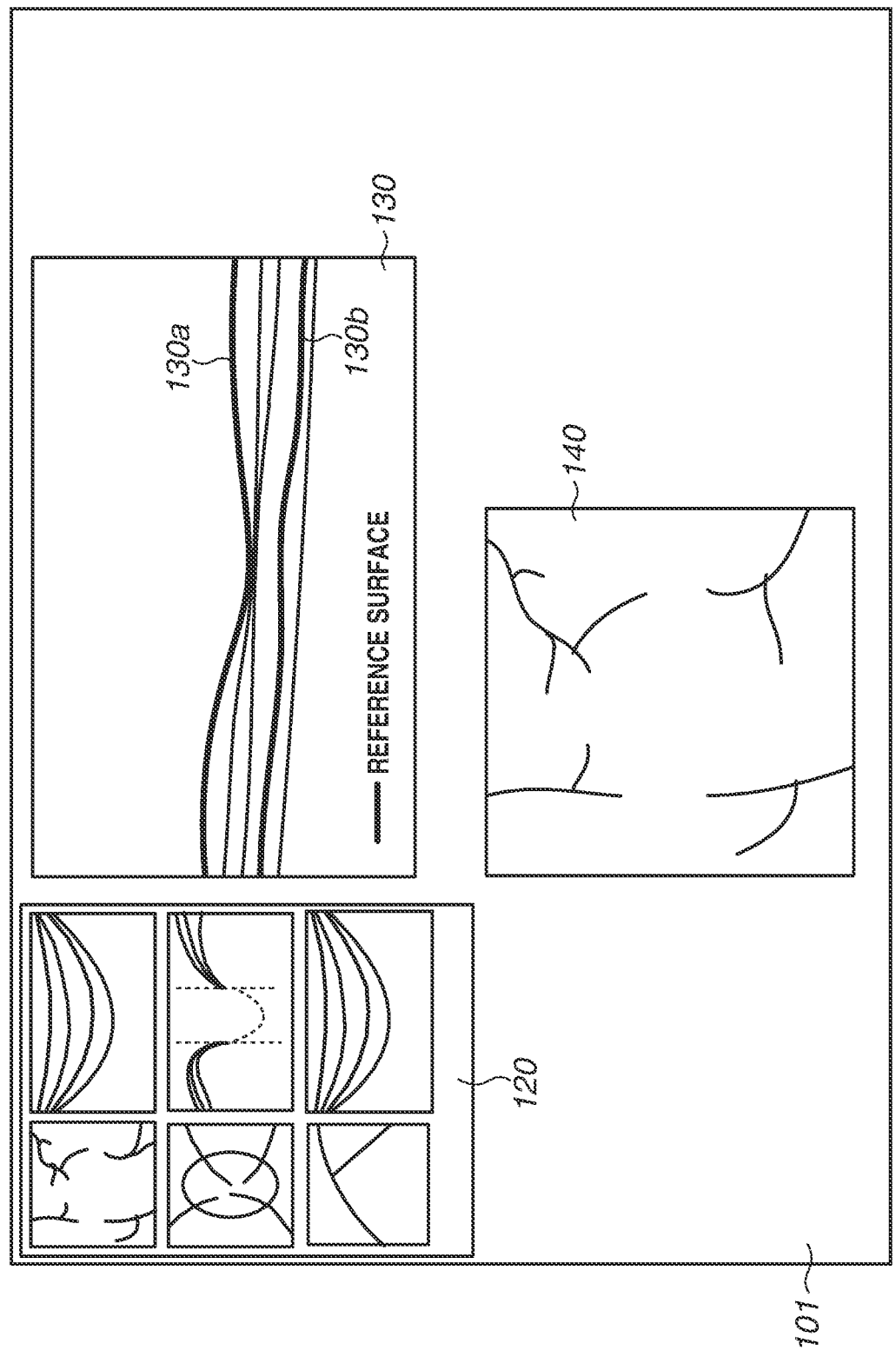
FIG. 7 is a diagram illustrating an example of a display screen of the image processing apparatus according to the first exemplary embodiment.

The image processing apparatus 209 generates, from a three-dimensional image, an en-face image that is a two-dimensional image projected to a plane based on any two reference surfaces in a depth direction (Z direction), for example. FIG. 7 illustrates an example of a B-scan image 130 and an en-face image 140 that are generated by the image processing apparatus 209. The en-face image 140 is an image acquired by projecting, to the Z direction, a range lying between a reference surface 130a and a reference surface 130b of the B-scan image 130. Specifically, as illustrated in FIG. 4, the image processing apparatus 209 extracts information in only a specific depth range of a three-dimensional image (not illustrated), structured from a plurality of acquired B-scan images 40-1 to 40-$n$. The image processing apparatus 20 then projects the information to an X-Y plane to generate the en-face image 140. Since an en-face image can be generated by using various known methods, detailed description thereof is omitted.

Figure 5:
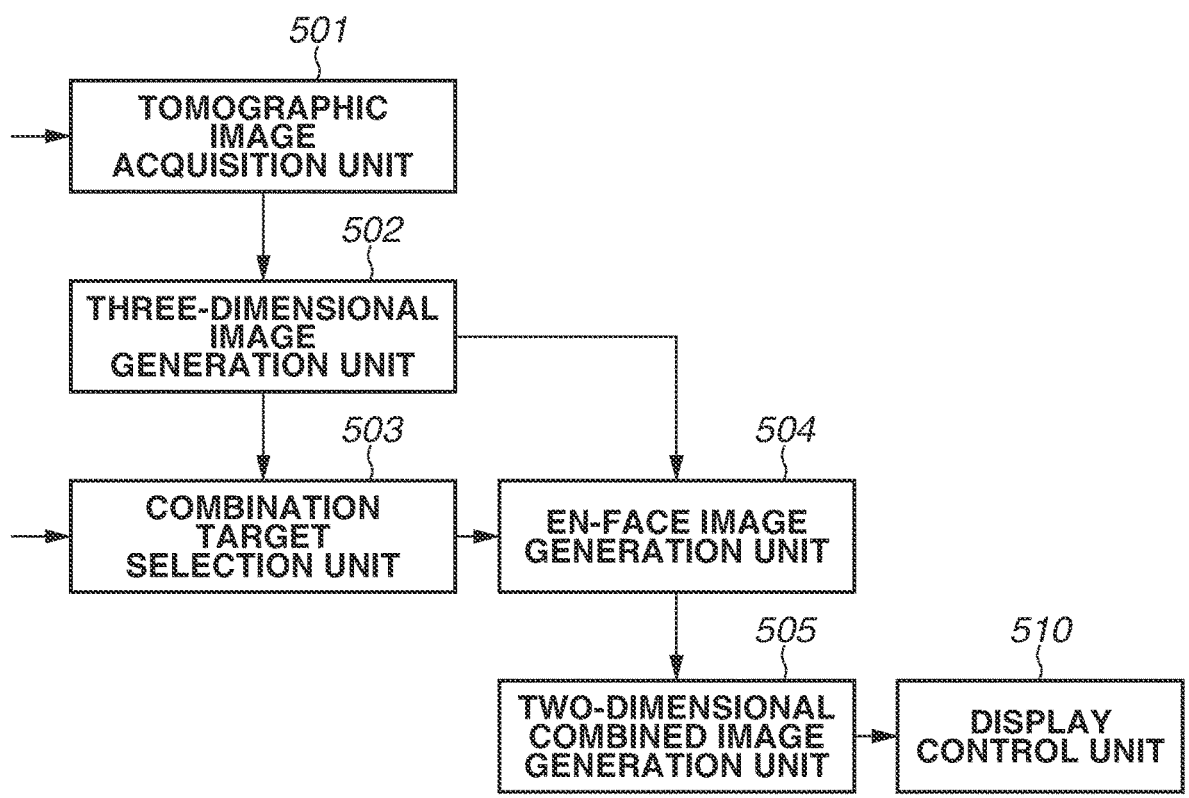
FIG. 5 is a block diagram illustrating an example of a configuration of the image processing apparatus according to the first exemplary embodiment.

An example of a configuration of the image processing apparatus 209 according to the present exemplary embodiment will be described below with reference to FIG. 5. The image processing apparatus 209 includes a tomographic image acquisition unit 501, a three-dimensional image generation unit 502, a combination target selection unit 503, an en-face image generation unit 504, a two-dimensional combined image generation unit 505, and a display control unit 510.

The image processing apparatus 209 includes a central processing unit (CPU) and a read-only memory (ROM) (not illustrated). The CPU executes a program stored in the ROM to function as the above-described respective units. The image processing apparatus 209 may include one CPU and one ROM or a plurality of CPUs and ROMs. In other words, in a case where at least one or more processors and at least one or more memories are connected, and the at least one or more processors execute programs stored in the at least one or more memories, the image processing apparatus 209 functions as the above-described respective units. The processor is not limited to the CPU, and may be a graphics processing unit (GPU), or different types of processors such as the CPU and the GPU may be used in combination.

The tomographic image acquisition unit 501 acquires tomographic images of a plurality of portions captured by the OCT image capturing apparatus 201. The tomographic image acquisition unit 501 may generate a tomographic image based on an output from the line sensor 208 to acquire the tomographic image. Alternatively, the tomographic image acquisition unit 501 may acquire a tomographic image that has been already generated from a database (not illustrated).

The three-dimensional image generation unit 502 generates a three-dimensional image based on the tomographic images of the plurality of portions acquired by the tomographic image acquisition unit 501. The three-dimensional image generation unit 502, for example, arrange the tomographic images of the plurality of portions on one coordinate system to generate a three-dimensional tomographic image. Further, the three-dimensional image generation unit 502 generates a motion contrast image (OCT angiography image) from a plurality of the tomographic images acquired for each portion, and arrange the motion contrast images generated for each portion on one coordinate system. In such a manner, the three-dimensional image generation unit 502 can also generate a three-dimensional motion contrast image. In other words, the three-dimensional image generation unit 502 generates a three-dimensional tomographic image (luminance tomographic image) or a three-dimensional motion contrast image as a three-dimensional image. Further, the en-face image generation unit 504 (described below) generates an en-face image of luminance or an en-face image of motion contrast as an en-face image from this three-dimensional image.

The combination target selection unit 503 selects a combination target for generating a two-dimensional combined image. The combination target may be automatically selected or may be selected in accordance with an instruction from an operator. The combination target selection unit 503 selects, for example, a three-dimensional image as the combination target.

The en-face image generation unit 504 sets any two surfaces at different depth positions to the three-dimensional image. The any two surfaces are reference surfaces when the en-face image is generated. The en-face image generation unit 504 generates the en-face image based on a region lying between the set two reference surfaces. The reference surfaces may be surfaces along a layer boundary included in the tomographic image or may be planes. For example, the en-face image generation unit 504 determines a representative value of pixel values in the depth direction at positions in the region lying between the two reference surfaces, and generates the en-face image based on the representative value. The representative value is an average value, a median value, or a maximum value of pixels in the depth direction of the region lying between the two reference surfaces. The en-face image generation unit 504 applies a uniform generation condition in the processing to all three-dimensional images of a plurality of combination targets selected by the combination target selection unit 503. In such a manner, a plurality of en-face images is acquired.

The two-dimensional combined image generation unit 505 aligns and combines the plurality of en-face images generated by the en-face image generation unit 504 to generate a two-dimensional combined image. The two-dimensional combined image generation unit 505 can perform the alignment using, for example, features of blood vessels included in the plurality of en-face images. Further, the two-dimensional combined image generation unit 505 can align the plurality of en-face images based on a lighting position of the fixation lamp during the capturing of the three-dimensional images as sources of the en-face images. Further, the two-dimensional combined image generation unit 505 may align the plurality of en-face image using the features of a blood vessel and a lighting position of the fixation lamp.

The display control unit 510, for example, causes the display apparatus 101 to display the generated two-dimensional combined image.

The display apparatus 101 is a liquid crystal display (LCD) apparatus or the like, and displays various information based on control by the display control unit 510. For example, as illustrated in FIG. 1, the display apparatus 101 displays an integrating image acquired by integrating pixel values of the three-dimensional images acquired by the capturing in the Z direction (depth direction) and a B-scan image in the display area 120. Further, the display apparatus 101 displays a two-dimensional combined image generated by the two-dimensional combined image generation unit 505 in a display area 111. An additionally provided optical system may display a scanning laser ophthalmoscope (SLO) image or the like captured simultaneously with the respective three-dimensional images and displayed in the display area 120 or an area that is not illustrated herein.

Figure 6:
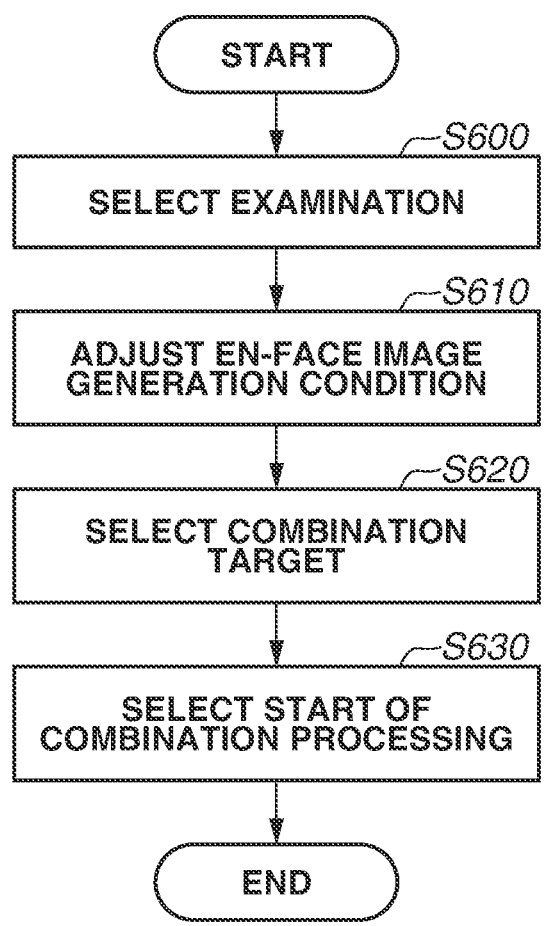
FIG. 6 is a flowchart illustrating an example of an operation of the image processing apparatus according to the first exemplary embodiment.
Figure 8:
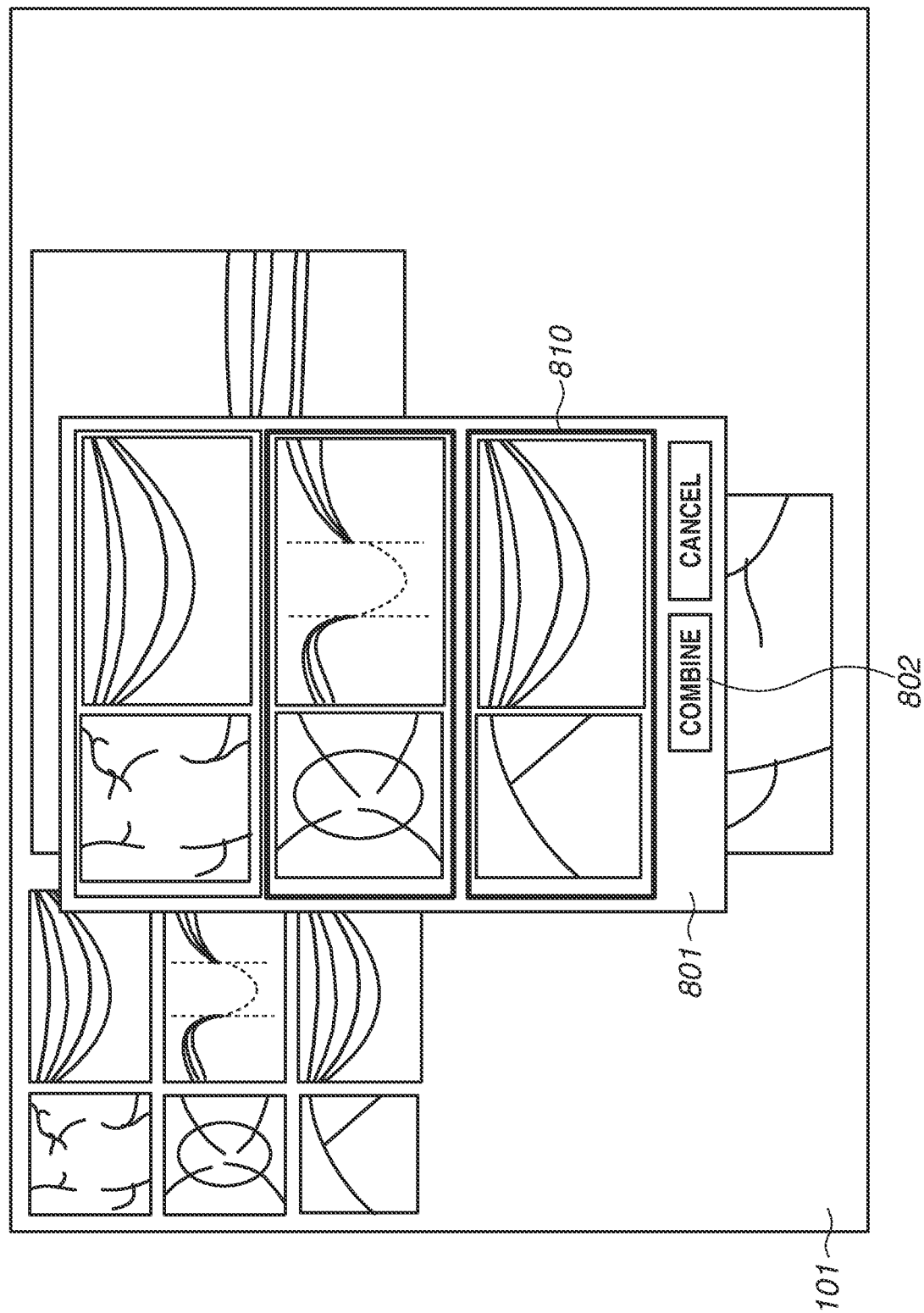
FIG. 8 is a diagram illustrating an example of a display screen of the image processing apparatus according to the first exemplary embodiment.

An example of an operation method and an operation of the image processing apparatus 209 will be described below with reference to FIG. 6 to FIG. 8. In the present exemplary embodiment, at least one of a three-dimensional tomographic image and a three-dimensional motion contrast image is saved for one examination. Further, in a case where an en-face image has been already generated, one examination includes, for example, an en-face image and a generation condition representing a depth range of the en-face image in a three-dimensional image. Thus, in the case where an en-face image is generated, the generation condition of the en-face image is associated with an examination including the en-face image and a three-dimensional image that is a source of the en-face image.

In step S600, an operator selects an examination. The display control unit 510 displays, for example as illustrated in FIG. 7, a B-scan image corresponding to the selected examination in the display area 130. Further, the display control unit 510 displays an en-face image generated from a three-dimensional image using a predetermined generation condition (a reference surface, a method for determining a representative value, and an artifact reduction processing) in the display area 140. More specifically, the en-face image generation unit 504 applies the predetermined generation condition stored in a memory or the like to the three-dimensional image included in the selected examination to generate an en-face image. The display control unit 510 causes the display apparatus 101 to display the generated en-face image on the display area 140. The en-face image to be displayed in the display area 140 may be generated from a three-dimensional motion contrast image or from a three-dimensional tomographic image.

In the present exemplary embodiment, the predetermined generation condition is used as the generation condition of the en-face image to be displayed in the selection of an examination by the operator, but the present invention is not limited to this. The operator may specify the generation condition in advance. Alternatively, a generation condition that is once set by the operator may be recorded in a recording device (not illustrated), and may be read automatically from the recording device to be applied during generation of an en-face image. In the present exemplary embodiment, the predetermined generation condition is, for example, that two reference surfaces are an internal limiting membrane and a pigmented layer of retina, a representative value is an average value between the reference surfaces, and the artifact reduction processing is not executed. In other words, the generation condition includes at least one of information representing a depth range in a three-dimensional image for generating an en-face image (e.g., position information about the two reference surfaces), a method for determining a representative value in a region lying between the two reference surfaces (depth range), and whether the artifact reduction processing is executed. An example of the artifact reduction processing includes processing for reducing projection artifact.

In step S610, the operator adjusts the generation condition of a displayed en-face image. For example, the operator changes the reference surfaces into a nerve fiber layer and a ganglion cell layer, and a representative value into a maximum value between reference surfaces. In a case where a specific generation condition does not have to be changed, this step may be omitted.

In a case where the generation condition is changed, the en-face image generation unit 504 generates an en-face image corresponding to the changed generation condition. The display control unit 510 updates the image in the display area 140 from the en-face image generated based on the predetermined generation condition into the en-face image generated based on the changed generation condition. A reference surface can be changed by using a known method. For example, the image processing apparatus 209 displays the reference surfaces 130*a* and the 130*b* on the B-scan image. The reference surfaces 130*a* and 130*b* can be acquired in such a manner that the image processing apparatus 209 analyzes a tomographic image to detect a layer boundary. In a case where the operator selects the reference surface 130*a* or 130*b* with a mouse and performs a vertical dragging operation, the image processing apparatus 209 moves the selected reference surface vertically to be able to change a position of the reference surface. In the present exemplary embodiment, the reference surface is moved with the mouse, but the present invention is not limited to this. For example, the image processing apparatus 209 detects a plurality of layer boundaries, and the operator may select any layer boundary from the plurality of detected layer boundaries or may specify a straight line horizontal to the B-scan image. The en-face image generated in step S600 or step S610 corresponds to an example of a first en-face image.

In step S620, the operator selects a target to be combined with the displayed en-face image. First, the operator selects a menu (not illustrated) in order to execute the combination processing. When the menu is selected, the display control unit 510 causes the display apparatus 101 to display an examination list 801 to be the combination target on a foreground, for example as illustrated in FIG. 8. The display control unit 510 causes the respective examinations to be displayed in the examination list 801, for example, in a method equal to the display method for the display area 120. The combination target selection unit 503 can select whether each of the examinations is the combination target in accordance with an instruction from the operator. The display control unit 510 causes, for example, an examination 810 selected as the combination target to be highlighted and displayed on the display apparatus 101 to notify the operator of a selected state. For example, as an examination to be the combination target, the display control unit 510 displays, in the list, an examination in which an imaged target eye, an imaging date, and an imaging size are identical to those in the examination selected in step S600, as an examination to be the combination target. In other words, the display control unit 510 causes the display apparatus 101 to display, as the examination list 801, the examination in which the imaged target eye, the imaging date, and the imaging size are the same as those in the examination already displayed on the display apparatus 101. Each examination is associated with identification information about a target eye (e.g., patient identification information and information representing whether an examination target is a left eye or right eye), and information such as an examination date and an imaging size. The display control unit 510 can cause, based on the identification information or the like, the display apparatus 101 to display the examination in which the imaged target eye, the imaging date, and the imaging size are the same as those in the examination already displayed on the display apparatus 101, as the examination list 801.

In the present exemplary embodiment, an examination conducted on the same date as an examination already displayed on the display apparatus 101 is displayed, but any examination conducted on the same target eye may be displayed even if the date is not the same. Further, the display apparatus 101 displays an examination in the same imaging size as that in the examination already displayed on the display apparatus 101, but the configuration is not limited to this. For example, an examination including a grainy image obtained by wide-angle imaging of the same target eye, can be the combination target. As a result, alignment becomes easy in some cases. Further, an examination in which imaging is detected as being failed due to blinking during the imaging may be set not to be displayed and thus does not become the combination target. For example, the image processing apparatus 209 can determine based on brightness of a tomographic image whether imaging is failed due to blinking during the imaging. If the image processing apparatus 209 determines that the imaging is failed, information representing failure may be associated with the examination. The display control unit 510 can determine, based on the information representing failure, whether the examination is to be displayed as the examination list 801.

The operator then selects an examination to be the combination target. In the present exemplary embodiment, in an initial state when the examination list 801 is displayed, an examination imaged in the panoramic imaging mode is displayed in a state where the examination is selected by the combination target selection unit 503. In other words, the display control unit 510 causes the display unit 101 to display the examination imaged in the panoramic imaging mode in a state where the examination is highlighted in the initial state of the examination list 801. Therefore, even in a case of the examination in which the imaged target eye, the imaging date, and the imaging size are identical to those in the examination selected in step S600, a display state in the initial state of the examination list 801 varies in accordance with whether the examination includes the image captured in the panoramic imaging mode. As a result, in a case of the imaging in the panoramic imaging mode, the operator can avoid the trouble of selecting the examination as the combination target. Herein, the panoramic imaging mode is an imaging mode in which a plurality of different portions of an eye part is imaged for generating a panoramic image. For example, this is a mode in which a display position of the fixation lamp is sequentially changed automatically or manually so that an image suitable for the panoramic image can be acquired, and the imaging is carried out at the display positions of the fixation lamp. Therefore, a plurality of three-dimensional images captured in the panoramic imaging mode corresponds to an example of a three-dimensional image acquired by imaging areas of a target eye at least partially different.

The information representing the imaging in the panoramic imaging mode is associated with a plurality of examinations in which the imaging is carried out in the panoramic imaging mode. The combination target selection unit 503 can select an examination in which the imaging is carried out in the panoramic imaging mode in the initial state of the examination list 801, based on the information representing the image captured in the panoramic imaging mode. Thus, the display control unit 510 can cause the display unit 101 to display the examination in which the imaging is carried out in the panoramic imaging mode in a state where the examination is highlighted in the initial state of the examination list 801, based on the information representing the image captured in the panoramic imaging mode. Only in a case where the examination selected in step S600 is imaged in the panoramic imaging mode, in the initial state of the examination list 801, the examination in which the imaging is carried out in the panoramic imaging mode may be highlighted and display on the display unit 101. If the examination selected in step S600 is not imaged in the panoramic imaging mode, in the initial state of the examination list 801, the examination in which the imaging is carried out in the panoramic imaging mode may not be highlighted.

In a case where the panoramic imaging is carried out more than once, the information representing the images captured in the panoramic imaging mode may be associated with the examinations, respectively, so that each panoramic imaging can be distinguished. The display control unit 510 may cause the display unit 101 to display each examination in the examination list 801 with each examination being highlighted so that the panoramic imaging carried out more than once can be distinguished from each other. For example, the display control unit 510 highlights a plurality of examinations relating to a first panoramic imaging using a frame of red, and highlights a plurality of examinations relating to a second panoramic imaging using a frame of any color other than red. The highlighting method is not limited to the above described example as long as the panoramic imaging carried out more than once can be distinguished from each other.

In the present exemplary embodiment, the display method for the examination list 801 is identical to the display method for the display area 120 but not limited thereto as long as respective imaging regions of the examinations can be distinguished from each other. For example, the display control unit 510 can cause the display apparatus 101 to display an en-face image generated based on the generation condition set in step S610 or a scanning laser ophthalmoscope (SLO) image. Alternatively, a B-scan image may be set not to be displayed. As a result, the operator can select a combination target while checking an image state of an examination as the combination target.

After selecting the examination as the combining object, in step S630, the operator selects a button 802 for notifying the image processing apparatus 209 of the start of the combination processing. If the button 802 is selected, the en-face image generation unit 504 acquires a predetermined generation condition of an en-face image or the generation condition of the en-face image changed in step S610 from the memory. For example, the changed generation condition of the en-face image is recorded in a memory associated with an examination. The en-face image generation unit 504 corresponds to an example of an acquisition unit that acquires a generation condition of a first en-face image generated from a first three-dimensional image of a target eye.

The en-face image generation unit 504 automatically applies the acquired generation condition to all three-dimensional images of examinations selected in step S620 to generate en-face images associated with the examinations. Herein, the en-face image generated in step S630 corresponds to an example of a second en-face image. Specifically, if a predetermined generation condition is not changed in step S610, the predetermined generation condition is automatically applied to all three-dimensional images of the examinations selected in step S620 to generate en-face images associated with the examinations. If the predetermined generation condition is changed in step S610, the changed generation condition of an en-face image is automatically applied to all three-dimensional images of the examinations selected in step S620 to generate en-face images associated with the examinations. Thus, the en-face image generation unit 504 corresponds to an example of a first generation unit that applies the generation condition acquired by the acquisition unit to a second three-dimensional image of a target eye to generate a second en-face image from the second three-dimensional image. More specifically, in a case where a user selects the first en-face image displayed on the display unit and the second three-dimensional image as a target of a combined image, the en-face image generation unit 504 corresponding to an example of the first generation unit applies the generation condition acquired by the acquisition unit to the second three-dimensional image of the target eye. In such a manner, the en-face image generation unit 504 generates the second en-face image.

Position information about the two reference surfaces included in the generation condition is, for example, information representing a name of a layer boundary. The image processing apparatus 209 applies a known layer boundary extracting technique to all the three-dimensional images of the examinations selected in step S620. In such a manner, the image processing apparatus 209 can recognize the layer boundary. Accordingly, the en-face image generation unit 504 applies the position information about the two reference surfaces relating to the displayed en-face image to all the images of the examinations selected in step S620. In such a manner, the en-face image generation unit 504 can generate the en-face image. Further, the image processing apparatus 209 may align the three-dimensional image as a source of the displayed en-face image with the three-dimensional images included in all the examinations selected in step S620. The en-face image generation unit 504 applies the position information about the two reference surfaces relating to the displayed en-face image to the images of the examinations selected in step S620, based on an alignment result. In such a manner, the en-face image generation unit 504 also can generate the en-face image.

The two-dimensional combined image generation unit 505 then aligns the plurality of generated en-face images to generate a two-dimensional panoramic combined image acquired by combining the plurality of en-face images, based on an alignment result. More specifically, the two-dimensional combined image generation unit 505 generates a two-dimensional panoramic combined image acquired by combining the en-face image generated in step S600 or S610 with the en-face image generated in step S630. In other words, the two-dimensional combined image generation unit 505 corresponds to an example of a second generation unit that generates a combined image by combining the first en-face image with the second en-face image.

Further, the display control unit 510 displays the generated two-dimensional panoramic combined image in the display area 111.

In the present exemplary embodiment, the operator selects the examination to be the combined target in step S620, but the configuration is not limited to this. For example, in step S610, the operator who has adjusted the generation condition for an en-face image may directly select the start of the combination processing in step S630. In this case, the combination target selection unit 503, for example, automatically selects the examination in which the imaging is carried out in the panoramic imaging mode. The two-dimensional combined image generation unit 505 can generate a two-dimensional panoramic combined image similarly to the above-described method.

In the present exemplary embodiment, as the generation condition of an en-face image to be applied automatically to all three-dimensional images to be combined, the generation condition including two reference surfaces, the representative value determining method, and whether the artifact reduction processing is executed is used. However, the generation condition is not limited to this condition. For example, the generation condition may not include whether the artifact reduction processing is applied. Further, for example, the generation condition may include luminance, contrast, a gamma curve, and a noise reduction method to be adjusted for causing an en-face image suitable for display. As a result, a sense of incongruity felt when a plurality of images with different luminance and contrasts is combined can be reduced.

In the present exemplary embodiment, only one en-face image is displayed on the display apparatus 101, but the display is not limited to this. The generation condition may be applied to, for example, an image processing apparatus that simultaneously displays en-face images generated under the generation conditions of a plurality of en-face images. In this case, the generation condition of an en-face image to be preferentially used for the combination processing is determined in advance, so that a two-dimensional panoramic combined image can be generated similarly to the above-described method. For example, the en-face image generation unit 504 applies the generation condition relating to an en-face image clicked (selected) from the plurality of en-face images displayed on the display apparatus 101 to all the images of the examinations selected in step S620. In such a manner, the en-face image generation unit 504 generates an en-face image.

According to the present exemplary embodiment described above, the generation condition of an en-face image specified for one three-dimensional image is automatically applied to all the three-dimensional images to be combined so that a two-dimensional panoramic combined image can be acquired. As a result, time and effort taken when the generation condition of an en-face image is set for the three-dimensional images to be combined can be simplified.

Further, as described in the present exemplary embodiment, when a two-dimensional panoramic combined image is acquired, en-face images are generated in advance and are combined. As a result, alignment and combining of three-dimensional images are not necessary, and thus the processing can be sped up.

The above-described method enables a two-dimensional combined image to be easily acquired from a plurality of three-dimensional images at a high speed.

A second exemplary embodiment will describe an example of a predetermined generation condition of an en-face image or an example of a case where in step S610, an operator sets the generation condition of an en-face image that the reference surfaces are retinal pigment epithelium and a lower end of an image, a representative value is a maximum value between the reference surfaces, and the artifact reduction processing is executed.

For example, in a motion contrast image of a portion lower than the retinal pigment epithelium, projection artifacts easily occur. The projection artifacts occurs in such a manner that a blood vessel identical to a blood vessel on an upper layer is drawn as a false blood vessel, or a shadow of the blood vessel on the upper layer is drawn in a motion contrast image of a periphery of an area with low luminance such as an external granular layer. For this reason, for example, in step S610, if an area lower than the retinal pigment epithelium (area on a choroid side) is specified as the generation condition of an en-face image, it is preferable that processing for reducing a projection artifact is executed. This processing can employ known various methods for correcting information about a blood vessel on a lower layer based on the information about the blood vessel on the upper layer.

Figure 9:
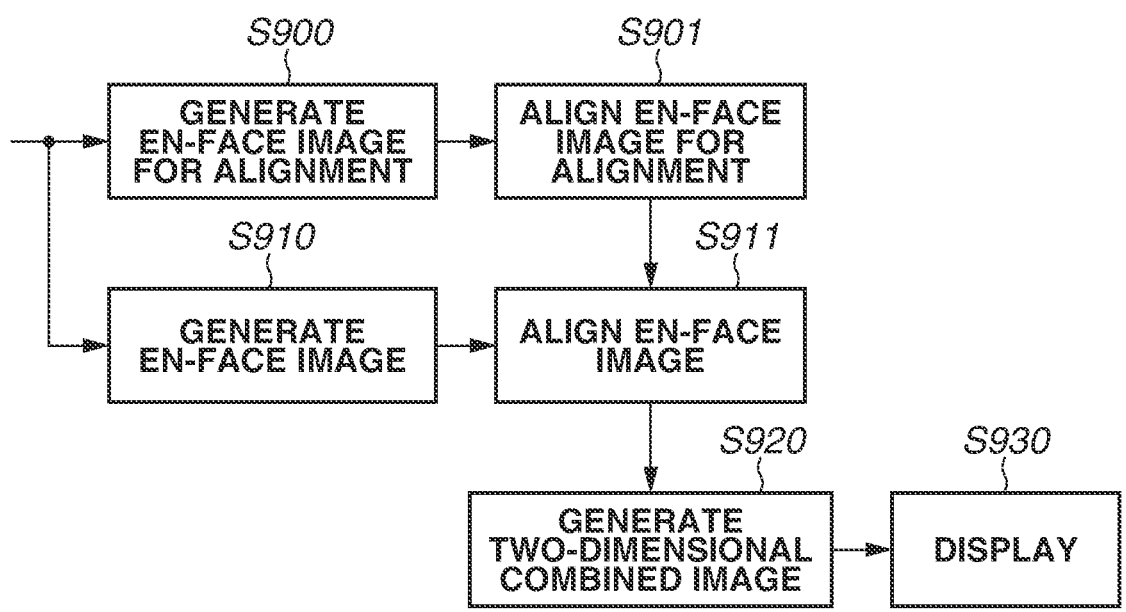
FIG. 9 is a diagram illustrating an example of an operation of an image processing apparatus according to a second exemplary embodiment.

FIG. 9 is a flowchart illustrating an example of an operation of the image processing apparatus 209 according to the second exemplary embodiment after the operator selects the button 802 in step S630. Since the operation flow for the operator and the configuration of the image processing apparatus 209 are similar to the operation flow and the configuration in the first exemplary embodiment, description thereof is omitted.

In step S900, for example, the en-face image generation unit 504 generates alignment en-face images with respect to the three-dimensional image of the examination selected in step S600 and all the three-dimensional images of the examinations selected in step S620. The alignment en-face images are used for the alignment to be carried out under such a condition that internal limiting membrane and a surface lower from a boundary between a ganglion cell layer and an inner plexiform layer by 50 μm are reference surfaces. The reference surfaces of the en-face images for the alignment are not limited to the above-described surfaces, and for example, any reference surfaces including the ganglion cell layer may be used. This is because a capillary network of a surface layer is present on the ganglion cell layer and the capillary network of the surface layer can be utilized for a reference of the alignment. In such a manner, the en-face image generation unit 504 corresponding to an example of the first generation unit generates a third en-face image and a fourth en-face image from a first three-dimensional image and a second three-dimensional image. The third and fourth en-face images are within a depth range including an area on a vitreous body side with respect to a depth range in the first three-dimensional image included in the generation condition. The third en-face image and the fourth en-face image correspond to an example of the en-face images for the alignment.

Further, the en-face images for alignment may be always generated. Alternatively, if the depth range represented by the predetermined generation condition of an en-face image or the generation condition changed in step S610 does not include the ganglion cell layer, the en-face image generation unit 504 may generate en-face images including the ganglion cell layer as the en-face images for alignment. More specifically, if the depth range in the first three-dimensional image included in the generation condition does not include the ganglion cell layer, the en-face image generation unit 504 corresponding to an example of the first generation unit generates the third en-face image and the fourth en-face image. If the depth range in the first three-dimensional image included in the generation condition includes the ganglion cell layer, the en-face image generation unit 504 corresponding to an example of the first generation unit does not generate the third en-face image and the fourth en-face image.

In step S910, the en-face image generation unit 504 generates en-face images to which the specified generation condition or the generation condition for an en-face image specified in step S610 is applied.

In step S901, the two-dimensional combined image generation unit 505 aligns the plurality of generated en-face images for alignment. The two-dimensional combined image generation unit 505 aligns the plurality of en-face images for alignment based on, for example, a blood vessel included in the en-face images for alignment. Thus, the two-dimensional combined image generation unit 505 acquires a misalignment amount of the plurality of en-face images for alignment.

In step S911, the two-dimensional combined image generation unit 505 aligns the plurality of en-face images generated in step S910, based on the alignment result in step S901. More specifically, the two-dimensional combined image generation unit 505 aligns the plurality of en-face images generated in step S910, based on the misalignment amount acquired in step S901.

In step S920, the two-dimensional combined image generation unit 505 generates a two-dimensional panoramic combined image based on the alignment result in step S910. In other words, the two-dimensional combined image generation unit 505 corresponding to an example of the second generation unit aligns the first en-face image and the second en-face image to generate a combined image based on the alignment result between the third en-face image and the fourth en-face image.

In step S930, the display control unit 510 causes the display apparatus 101 to display the generated two-dimensional panoramic combined image.

In the motion contrast image, a blood vessel on an upper layer such as a retina superficial layer is easily drawn, whereas a blood vessel on a lower layer such as a choroid coat is not drawn due to a noise in some cases. For this reason, as in the present exemplary embodiment, en-face images on which the blood vessel on the upper layer is drawn are used for the alignment between the en-face images. Therefore, the alignment can be carried out accurately regardless of the predetermined generation condition of an en-face image or the generation condition of an en-face image specified in step S610.

In the present exemplary embodiment, the en-face images on which the blood vessel on the retina superficial layer is drawn are used for the alignment, but the en-face images are not limited to them. For example, even if the above-described integrated images or SLO images are used for the alignment, the equivalent effect can be obtained.

According to the present exemplary embodiment described above, the two-dimensional panoramic combined image which is aligned accurately and has desirable reference surfaces can be generated using a simple method.

In the description, the present exemplary embodiment is applied to the case where the generation condition is such that the reference surfaces are retinal pigment epithelium and the lower end of the image, the representative value is the maximum value between the reference surfaces, and the artifact reduction processing is executed. However, the case to which the present exemplary embodiment is applied is not limited to the above case of the generation condition. For example, in a case where the depth range included in the generation condition does not include the ganglion cell layer, the en-face images for alignment may be generated.

The first exemplary embodiment has described the case where the two-dimensional panoramic combined image is generated as the combined image. However, a third exemplary embodiment will describe a case where an image is generated as the combined image by averaging a plurality of en-face images generated from a plurality of three-dimensional images of an approximately the same portion.

A tomographic image captured by the OCT image capturing apparatus 201 and a motion contrast image generated based on the tomographic image includes a noise component such as a speckle noise in some cases. As a noise reduction method, an average value filtering method is known, but if averaging is performed in one image by using an average value filter, there may be a worry that a resolution of the image is deteriorated. On the other hand, since the speckle noise is generated randomly, averaging a plurality of en-face images obtained by imaging an approximately same portion enables the noise to be reduced while maintaining the resolution of the image. In the present exemplary embodiment, this processing is referred to as combination processing.

The OCT image capturing apparatus 201 according to the present exemplary embodiment has a same portion imaging repetition mode as a mode for continuously acquiring tomographic images of an approximately same portion of a target eye. If the operator who desires to image the partial region 301 (see FIG. 3) of the target eye selects this mode, the OCT image capturing apparatus 201 does not change an imaging condition such as the position of the internal fixation lamp and an imaging size after the imaging of the partial region 301 is completed. Thus, the partial region 301 can be again imaged under the same condition. The tomographic image acquisition unit 501 can acquire a plurality of tomographic images that approximately matches with the partial region 301 by the OCT image capturing apparatus 201 repeating the imaging desired number of times.

The operation to be performed by the operator according to the present exemplary embodiment is similar to the operation according to the first exemplary embodiment. The operation of the image processing apparatus 209 corresponding to the operation to be performed by the operator will be described.

In step S600, when the operator selects a menu (not illustrated), in order to execute the combination processing, the display control unit 510 causes the display apparatus 101 to display the examination list 801 to be the combination target on a foreground similarly to the first exemplary embodiment. Further, in step S600, one examination is selected, and thus an en-face image or the like is displayed on the display apparatus 101. As the examination to be the combination target, the display control unit 510 causes the display apparatus 101 to display, in form of a list, examinations in which a target eye identical to that in the examinations selected in step S600 is imaged. The operator then selects an examination to be the combing target from the examination list 801. In the present exemplary embodiment, in an initial state where the examination list 801 is displayed, the display control unit 510 displays examinations in which the imaging is performed in the same portion imaging repetition mode in a state that the combination target selection unit 503 is selecting the examination. As a result, if the imaging is performed in the same portion imaging repetition mode, time and effort taken by the operator to select the examinations to be the combination targets can be reduced. The plurality of examinations in which the imaging is performed in the same portion imaging repetition mode is associated with information representing the imaging in the same portion imaging repetition mode. The combination target selection unit 503 can select the examinations in which the imaging is performed in the same portion imaging repetition mode in the initial state of the examination list 801, based on the information representing the imaging in the same portion imaging repetition mode. In other words, the display control unit 510 can highlight the examinations in which the imaging is performed in the same portion imaging repetition mode to cause the display unit 101 to display the examinations in the initial state of the examination list 801, based on the information representing the imaging in the same portion imaging repetition mode.

The operator who has selected the examinations to be the combination targets selects, in step S630, the button 802 for notifying the image processing apparatus 209 of the start of the combination processing. After the selection of the button 802, the en-face image generation unit 504 automatically applies the predetermined generation condition for generating an en-face image or the generation condition for an en-face image specified in step S610 to all images of the examinations selected in step S620. In such a manner, the en-face image generation unit 504 generates the en-face images corresponding to the respective examinations. The two-dimensional combined image generation unit 505 then aligns the plurality of generated en-face images, and combines the plurality of en-face images to generate a two-dimensional combined image (averaged image) based on the alignment result. Further, the display control unit 510 displays the generated two-dimensional combined image on the display area 111. The image generated in such a manner can be expected to have less noise than each of the images of the examinations.

According to present exemplary embodiment described above, the two-dimensional combined image where noise of the plurality of three-dimensional images are reduced can be acquired at high speed using a simple method.

A fourth exemplary embodiment will describe an example of the operation of the image processing apparatus 209 in a case where after the operator acquires the two-dimensional combined image in step S630, the processing returns to step S610 again, and en-face images are generated under a different generation condition.

Examples of the operating method and the operation of the image processing apparatus 209 according to the present exemplary embodiment will be described with reference to FIGS. 10 and 11. As illustrated in FIG. 10, the display apparatus 101 according to the present exemplary embodiment displays the panoramic combined image display area 111, the captured image list display area 120, the selected examination B-scan image display area 130, and the en-face image display area 140 on one screen. Since the processing in steps S600 to S630 in FIG. 11 to be executed first are similar to the processing in the first exemplary embodiment, detailed description thereof is omitted. At least one of the examination (three-dimensional image) selected in step S620 and information representing the misalignment of the plurality of en-face images acquired in step S630 is stored in the memory (not illustrated) of the image processing apparatus 209.

First, the processing after step S630 will be described. If the operator observes the combined image generated in step S630 and changes the generation condition of the en-face images used for combining, the processing returns to step S610, and the operator again adjusts the generation condition of the en-face images.

The operator who has adjusted the generation condition selects a menu (not illustrated) in step S630 in order to execute the combination processing again. This menu includes a user interface (UI) that can instruct the recombining. In the present exemplary embodiment, the operator can select the recombining, to execute the combination processing without reselecting a combination target examination on the examination list 801. For example, if the recombining is instructed, the combination target selection unit 503 acquires an examination (three-dimensional image) selected first in step S620 from the memory. The en-face image generation unit 504 then regenerates en-face images using the adjusted combining condition for images of combination target examinations identical to the images in the first combination processing. At this time, the combination target examinations include the examination selected in step S600. The two-dimensional combined image generation unit 505 aligns the plurality of en-face images. The two-dimensional combined image generation unit 505 can execute the processing based on the information representing the misalignment of the plurality of en-face images acquired first in step S630. As a result, the time for the alignment processing can be shortened.

After the alignment processing, the two-dimensional combined image generation unit 505 generates a two-dimensional panoramic combined image or an averaged image similarly to the first processing. The display control unit 510 displays the generated combined image in the display area 111 and saves the combined image on the memory (not illustrated).

The present exemplary embodiment can produce an effect similar to an effect of the first exemplary embodiment. Further, the second and subsequent image selection and alignment processing in the combination target processing are executed based on the results of the first image section and alignment processing, so that the processing time can be shortened.

The above-described first to fourth exemplary embodiments may be suitably combined. For example, the second and third exemplary embodiments may be combined. More specifically, the second exemplary embodiment may be applied to the alignment in a case where an image acquired by averaging the plurality of en-face images is generated as an example of the combined image other than the panoramic combined image.

Further, the second exemplary embodiment may be applied to the fourth exemplary embodiment. For example, the information representing the misalignment of the plurality of en-face images acquired first in step S630 may be acquired by the en-face images including the ganglion cell layer.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-171188, filed Sep. 6, 2017, which is hereby incorporated by reference herein in its entirety.

What is claimed is:

1. An image processing apparatus comprising:
a first generation unit configured to generate (a) a first en-face image by applying a generation condition to a first three-dimensional image of a subject, (b) a second en-face image by applying the generation condition to a second three-dimensional image of the subject, (c) a third en-face image using a part of the first three-dimensional image, and (d) a fourth en-face image using a part of the second three-dimensional image,
wherein the third en-face image and the fourth en-face image correspond to a depth range located closer to a vitreous body side than a depth range included in the generation condition; and
a second generation unit configured to generate a combined image by using the first en-face image, the second en-face image, and a result of alignment between the third en-face image and the fourth en-face image.

2. The image processing apparatus according to claim 1, wherein the first generation unit generates, in a case where the first en-face image displayed on a display unit is selected by a user and the second three-dimensional image is selected as a target of the combined image, the second en-face image by applying the generation condition to the second three-dimensional image of the subject.

3. The image processing apparatus according to claim 1, wherein the generation condition includes at least one of a depth range of the first en-face image in the first three-dimensional image, a method for determining a representative value of a pixel in the depth range, and whether artifact reduction processing is executed.

4. The image processing apparatus according to claim 1, wherein the first three-dimensional image and the second three-dimensional image are three-dimensional images obtained by imaging areas of the subject at least different in part, and
wherein the combined image is a panoramic image of the first en-face image and the second en-face image.

5. The image processing apparatus according to claim 1, wherein the first three-dimensional image and the second three-dimensional image are obtained by imaging areas of approximately same portions of the subject, and
wherein the combined image is obtained by averaging the first en-face image and the second en-face image.

6. The image processing apparatus according to claim 1, wherein the second generation unit aligns the first en-face image with the second en-face image using the result of alignment between the third en-face image and the fourth en-face image to generate the combined image.

7. The image processing apparatus according to claim 6, wherein the first generation unit generates, in a case where the depth range in the first three-dimensional image included in the generation condition does not include a ganglion cell layer, the third en-face image and the fourth en-face image.

8. The image processing apparatus according to claim 7, wherein the first generation unit does not generate, in a case where the depth range in the first three-dimensional image included in the generation condition includes the ganglion cell layer, the third en-face image and the fourth en-face image.

9. The image processing apparatus according to claim 1, wherein the three-dimensional image is a three-dimensional tomographic image obtained by using optical coherence tomography.

10. The image processing apparatus according to claim 1, wherein the three-dimensional image is a three-dimensional motion contrast image based on a tomographic image obtained by using optical coherence tomography.

11. The image processing apparatus according to claim 1, wherein the subject is an eye, and
wherein the depth range is obtained using a result of detection of a layer boundary in the first three-dimensional image and the second three-dimensional image.

12. A system comprising:
an optical coherence tomography image capturing apparatus that includes a detector configured to detect, as an interference signal, interference light obtained by combining return light and reference light, the return light returning from a subject irradiated with measurement light; and
the image processing apparatus according to claim 1, further comprising an obtaining unit configured to obtain the first three-dimensional image and the second three-dimensional image by using the detected interference signal.

13. An image processing method comprising:
generating (a) a first en-face image by applying a generation condition to a first three-dimensional image of a subject, (b) a second en-face image by applying the generation condition to a second three-dimensional image of the subject, (c) a third en-face image using a part of the first three-dimensional image, and (d) a fourth en-face image using a part of the second three-dimensional image,
wherein the third en-face image and the fourth en-face image correspond to a depth range closer to a vitreous body side than a depth range included in the generation condition; and
generating a combined image by using the first en-face image, the second en-face image, and a result of alignment between the third en-face image and the fourth en-face image.

14. A non-transitory computer-readable storage medium storing a program that when run on a computer causes the computer to execute the image processing method according to claim 13.

* * * * *